United States Patent
Lam et al.

(10) Patent No.: US 9,433,360 B2
(45) Date of Patent: Sep. 6, 2016

(54) ADJUSTABLE FINGER CUFF ASSEMBLY FOR A BLOOD PRESSURE MEASUREMENT DEVICE

(71) Applicant: CalHealth, Inc., Irvine, CA (US)

(72) Inventors: Phillip L. Lam, Monterey Park, CA (US); Ping Cheng Benjamin Liu, San Gabriel, CA (US)

(73) Assignee: CalHealth, Inc., Irvine, CA (US)

( * ) Notice: Subject to any disclaimer, the term of this patent is extended or adjusted under 35 U.S.C. 154(b) by 481 days.

(21) Appl. No.: 13/772,690

(22) Filed: Feb. 21, 2013

(65) Prior Publication Data

US 2013/0226015 A1    Aug. 29, 2013

Related U.S. Application Data

(60) Provisional application No. 61/634,099, filed on Feb. 23, 2012.

(51) Int. Cl.
*A61B 5/022* (2006.01)
*A61B 5/00* (2006.01)

(52) U.S. Cl.
CPC ......... *A61B 5/02241* (2013.01); *A61B 5/6897* (2013.01)

(58) Field of Classification Search
CPC .... A61B 5/02; A61B 5/021; A61B 5/02141; A61B 5/022; A61B 5/02233; A61B 5/02241
See application file for complete search history.

(56) References Cited

U.S. PATENT DOCUMENTS

| | | | | |
|---|---|---|---|---|
| 3,935,984 | A * | 2/1976 | Lichowsky et al. | 600/499 |
| 5,107,848 | A * | 4/1992 | Oku | 600/499 |
| 7,066,890 | B1 * | 6/2006 | Lam et al. | 600/485 |

* cited by examiner

*Primary Examiner* — Charles A Marmor, II
*Assistant Examiner* — Thaddeus Cox

(57) ABSTRACT

Finger cuff adjustability is provided in a measurement cylinder assembly in a unique manner which accommodates the size and space limitations inherent in a mouse-based blood pressure measurement device. The exterior radial surface of the inflatable cuff is adhered to a pull-tab which is longer than the cuff length and has a tab end channeled through a pair of rings, one of which is fixed or stationary and the other of which is an adjustment ring. Rotation of the adjustment ring either pulls or pushes the tab end through a slit in the fixed or stationary ring depending upon the direction of ring rotation. Pulling the tab end causes the adhered finger cuff to forcefully collapse around the user's finger in firmer engagement therewith and to compensate for a finger of smaller diameter. Pushing the tab end causes the adhered finger cuff to forcefully open to a larger profile to loosen the engagement with a finger and to compensate for a finger of larger diameter.

10 Claims, 7 Drawing Sheets

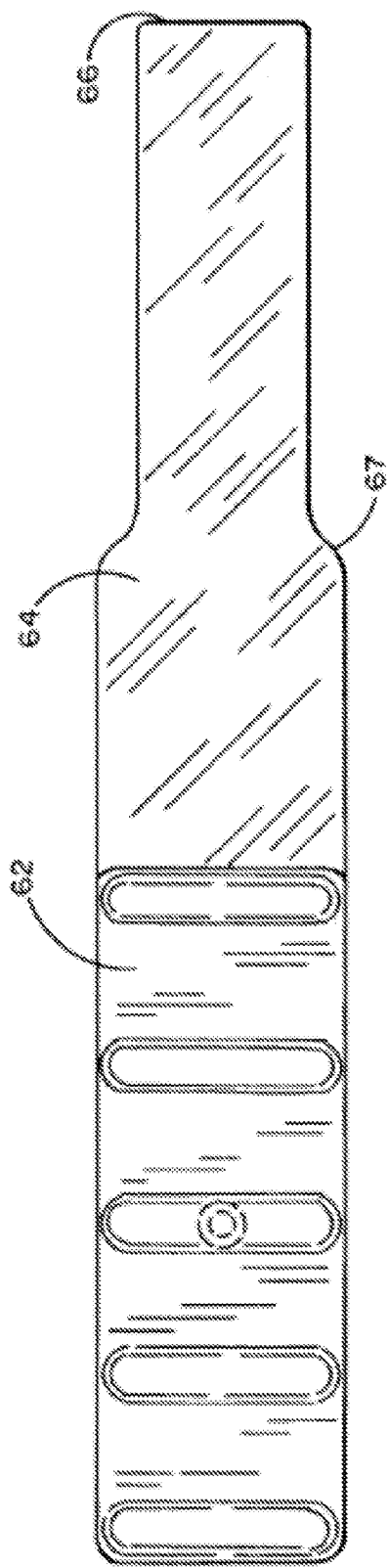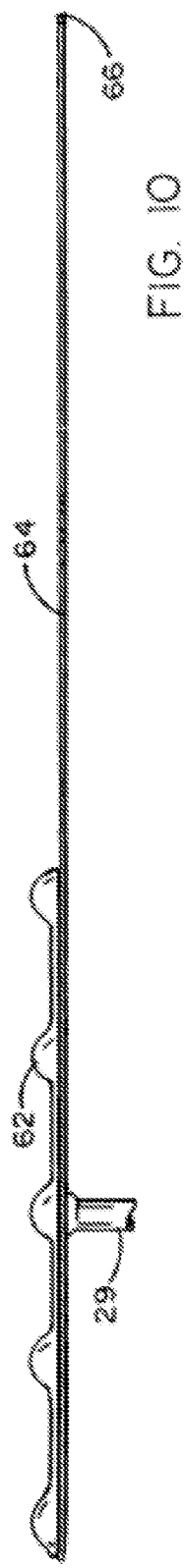

ADJUSTABLE FINGER CUFF ASSEMBLY FOR A BLOOD PRESSURE MEASUREMENT DEVICE

CROSS-REFERENCE TO RELATED APPLICATIONS

This application takes priority from U.S. Provisional Patent Application Ser. No. 61/634,099 filed Feb. 23, 2012.

BACKGROUND OF THE INVENTION

1. Field of the Invention

The present invention relates to a blood pressure measurement device of the type disclosed in issued U.S. Pat. No. 7,066,890. More specifically, the invention herein relates to an adjustable finger cuff assembly which in one embodiment extends from the interior of a computer mouse controller and in another embodiment plugs into ports in a computer mouse controller.

2. Background Art

The inventors herein are also the inventors of a combined computer mouse controller and blood pressure measurement device or sphygmomanometer described in the aforementioned U.S. Patent. In one disclosed embodiment of that invention, a blood pressure measurement device having an inflatable finger cuff, is stored inside an otherwise standard computer mouse controller. When it is desired to make a blood pressure measurement, an access panel is opened and a hinged measurement cylinder is rotated from an interior compartment to an exterior position alongside the mouse where a user can place his or her index finger through the hollow cylinder where it is at least partially surrounded by an inflatable cuff. In another embodiment, a similar measurement cylinder is simply attached to the side of the mouse to connect at least one plug to a corresponding port. In both embodiments, once the cylinder is in position for the blood pressure measurement, an air pump within the mouse inflates the cuff to occlude blood vessels within the finger and then air pressure is released gradually to detect the pressure when blood begins to flow again (systolic) and when blood flows freely (diastolic) using an oscillometric method of blood pressure measurement.

The applicants herein have found that in order to compensate for different finger diameters of many potential users, it is highly advantageous to provide a finger cuff adjustment feature which permits a user to alter the initial engagement pressure of the finger and cuff before the measurement is performed. Such an adjustment capability enables the inflation and deflation of the cuff to be over a reasonably uniform range of air pressure irrespective of finger size. While such variation in finger cuff engagement has been provided in prior art finger cuff blood pressure measurement devices (see for example the OMRON™ model 815f finger cuff measurement device), such adjustability in a mouse-based finger cuff assembly presents unique size and space limitations which are far more difficult to overcome.

SUMMARY OF THE INVENTION

In a preferred embodiment of the present invention, finger cuff adjustability is provided in a measurement cylinder assembly in a unique manner which accommodates the size and space limitations inherent in a mouse-based blood pressure measurement device. The exterior radial surface of the inflatable cuff is adhered to a pull-tab which is longer than the cuff length and has a tab end channeled through a pair of rings, one of which is fixed or stationary and the other of which is an adjustment ring. Rotation of the adjustment ring either pulls or pushes the tab end through a slit in the fixed or stationary ring depending upon the direction of ring rotation, Pulling the tab end causes the adhered finger cuff to forcefully collapse around the user's finger in firmer engagement therewith and to compensate for a finger of smaller diameter, Pushing the tab end causes the adhered finger cuff to forcefully open to a larger profile to loosen the engagement with a finger and to compensate for a finger of larger diameter. The preferred finger cuff cylinder assembly also provides an indexing flange at one axial end of the adjustment ring so that each user may remember his or her preferred adjustment position. A ratchet-type flange provided at the opposite end of the fixed ring, has a scalloped edge which cooperates with a locking lobe on the adjustment ring to retain the adjusted ring in its preferred position where the cuff engagement is best for a particular user.

BRIEF DESCRIPTION OF THE DRAWINGS

The aforementioned objects and advantages of the present invention, as well as additional objects and advantages thereof, will be more fully understood herein after as a result of a detailed description of a preferred embodiment when taken in conjunction with the following drawings in which:

FIGS. 9 and 10 are top and side views, respectively, of the inflatable finger cuff and adhered pull tab shown removed from the cylinder assembly and in a flat and laid out configuration.

DETAILED DESCRIPTION OF THE PREFERRED EMBODIMENTS

Figure 2:
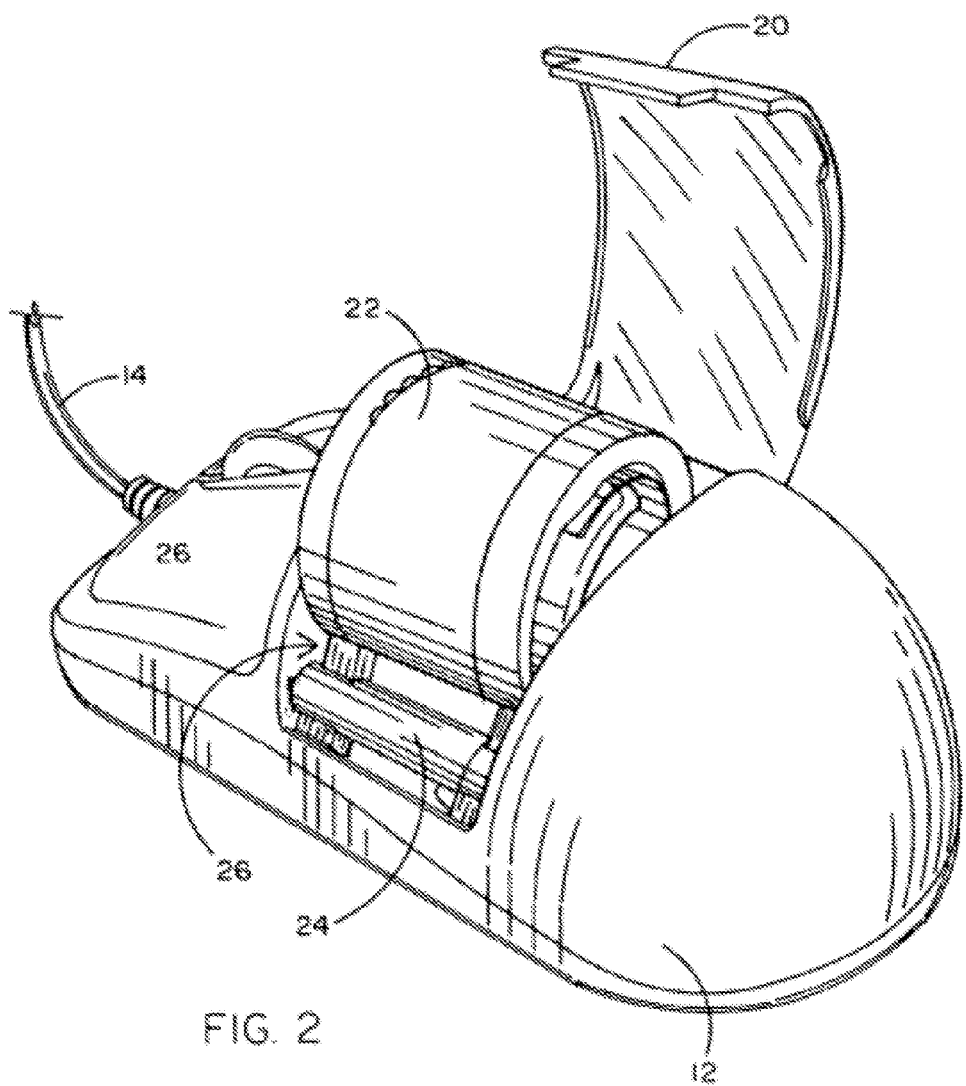
FIG. 2 is a view of the device of FIG. 1, but showing the access panel thereof opened and the cylinder assembly partially rotated out of the mouse compartment.
Figure 3:
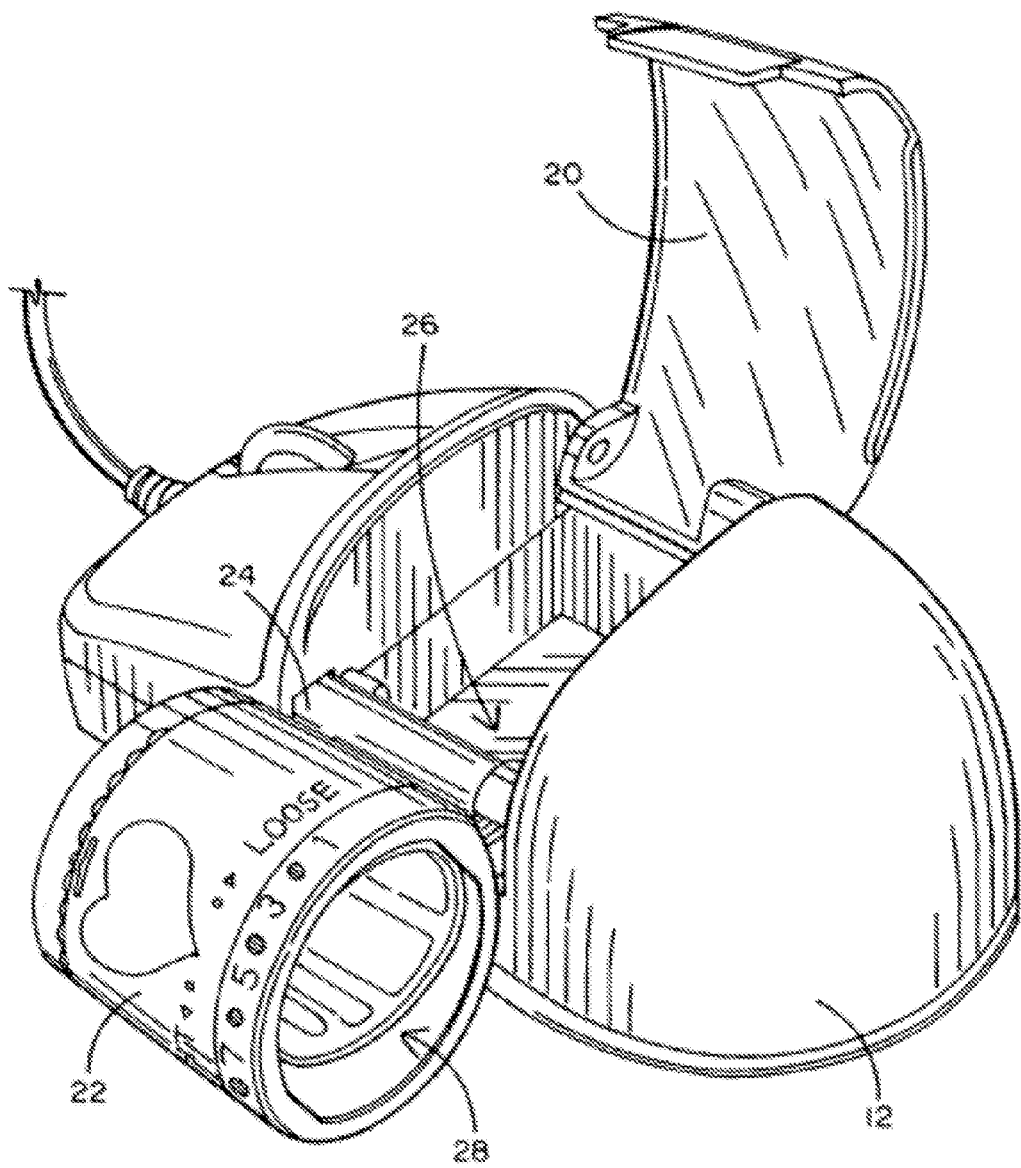
FIG. 3 is a view similar to that of FIGS. 1 and 2, but showing the cylinder assembly fully rotated out of the mouse compartment.

Referring to the accompanying figures it will be seen that a preferred embodiment of a combined mouse controller and blood pressure measurement device 10 comprises a mouse body 12 affixed to a USB cable 14 and having standard click buttons 16 and wheel control 18 and a unique hinged access panel 20. Panel 20, which may preferably be transparent or translucent, encloses an interior chamber or compartment 26 which permits storage of a blood pressure measurement cylinder assembly 22. As seen best in FIGS. 2 and 3, once the access panel 20 is hingedly opened, cylinder assembly 22 may be rotated out of compartment 26 about hinge 24 until the cylinder assembly is fully extended outside the mouse body 12 where the cylinder interior 28 is positioned to receive a user's finger for measurement of blood pressure.

Figure 1:
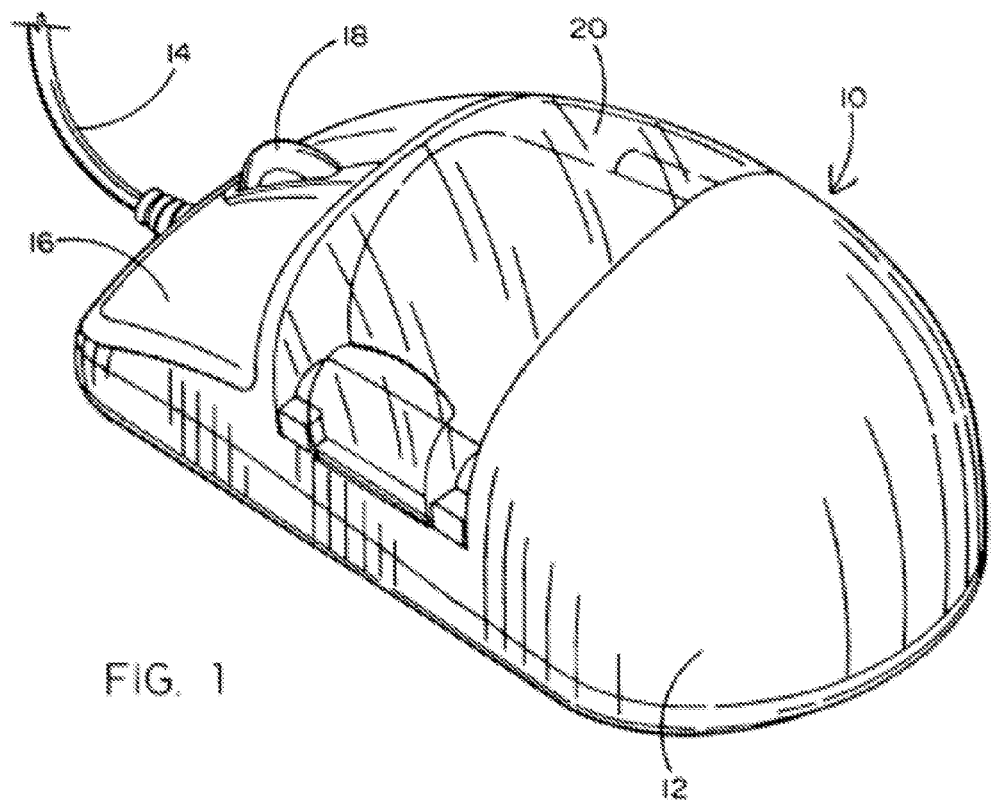
FIG. 1 is a three-dimensional view of a preferred embodiment of a mouse-based blood pressure measurement device with an internally stored finger cuff cylinder assembly.
Figure 4:
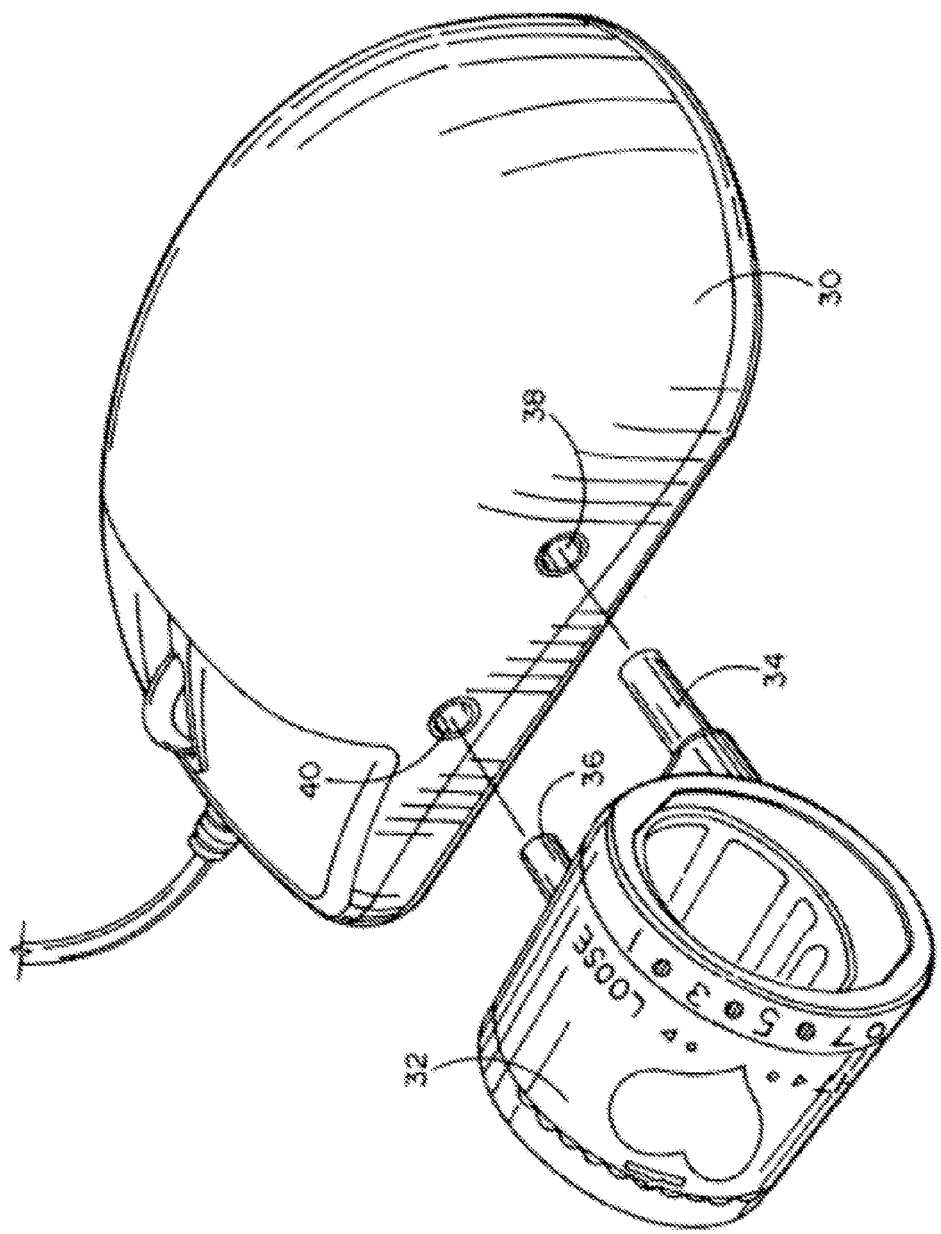
FIG. 4 is a three-dimensional view of an alternative embodiment where the finger cuff cylinder assembly and the mouse controller are configured to plug the cylinder into ports on the side of the mouse body.
Figure 5:
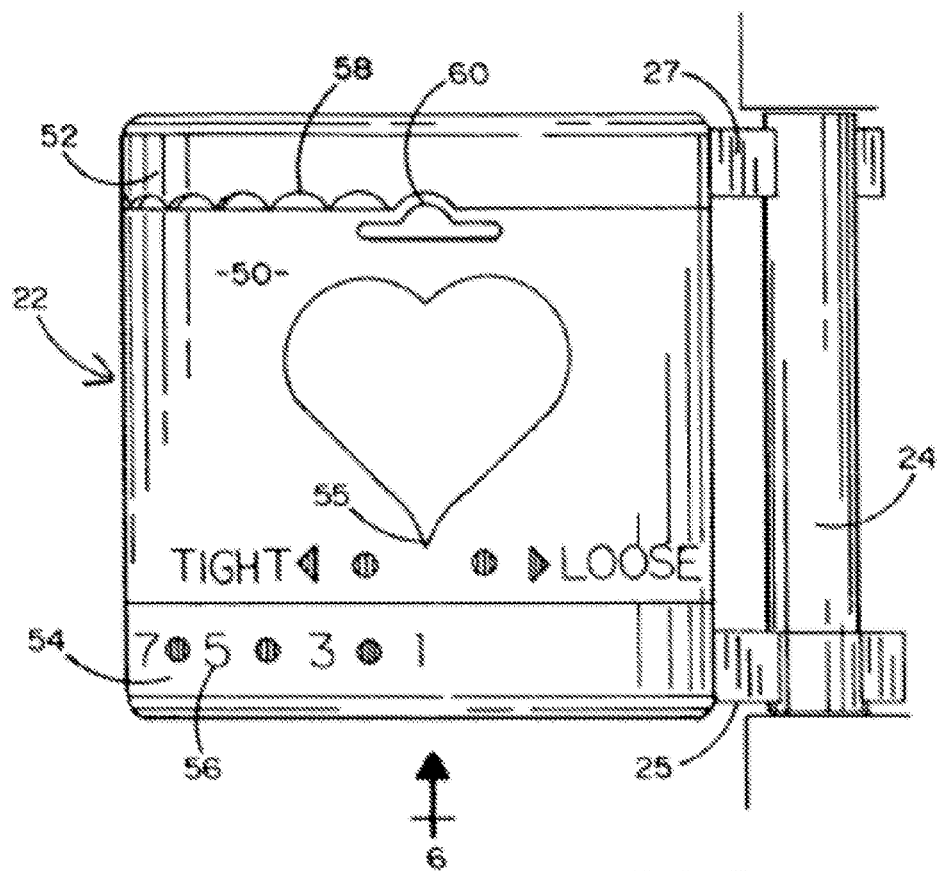
FIGS. 5 and 6 are top and end views, respectively, of the finger cuff cylinder assembly of the preferred embodiment shown in its fully opened configuration.

FIG. 4 illustrates an alternative configuration wherein a mouse controller body 30 receives an externally provided cylinder assembly 32. Assembly 32 has plugs 34 and 36 which are received in ports 38 and 40, respectively, in the side of body 30. Once so connected, cylinder assembly 32 of the embodiment of FIG. 4 operates in precisely the same way as cylinder assembly 22 of the embodiment of FIGS. 1 to 3 as will be described in conjunction with FIGS. 5 to 10.

As seen in FIGS. 5 to 10, assembly 22 comprises a pair of stem connections 25 and 27, each respectively molded to an opposed end of hinge 24. Inside stem 25 is an air tube 29 which extends into assembly 22 and connects to an inflatable finger cuff 62 to provide inflation and deflation of the cuff during each blood pressure measurement. Cylinder assembly 22 is formed of three ring-shaped components, namely, adjustment ring 50, locking flange 52 and indexing flange 54. Flange 54 has a plurality of numerical indicia 56 which correspond to pointer 55 on ring 50 to denote the relative position of the ring. Locking flange 52 has a scalloped edge 58 which cooperates with locking lobe 60 of ring 50 to provide a ratchet effect during rotation of ring 50 and a light locking effect to hold the ring in a selected rotated position. Flange 52 extends from an inner fixed cylinder or ring 57 on which ring 50 rests coaxially.

Figure 6:
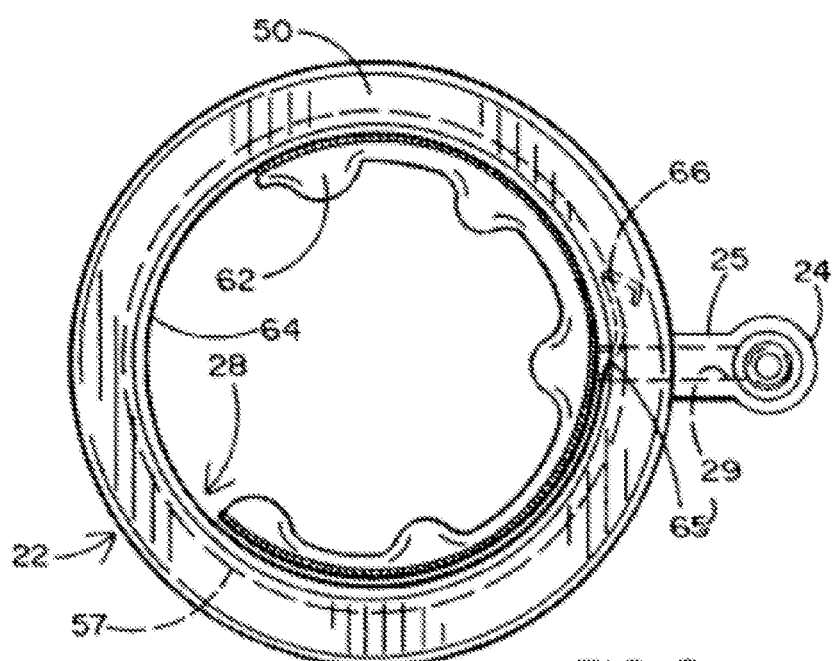
Figure 7:
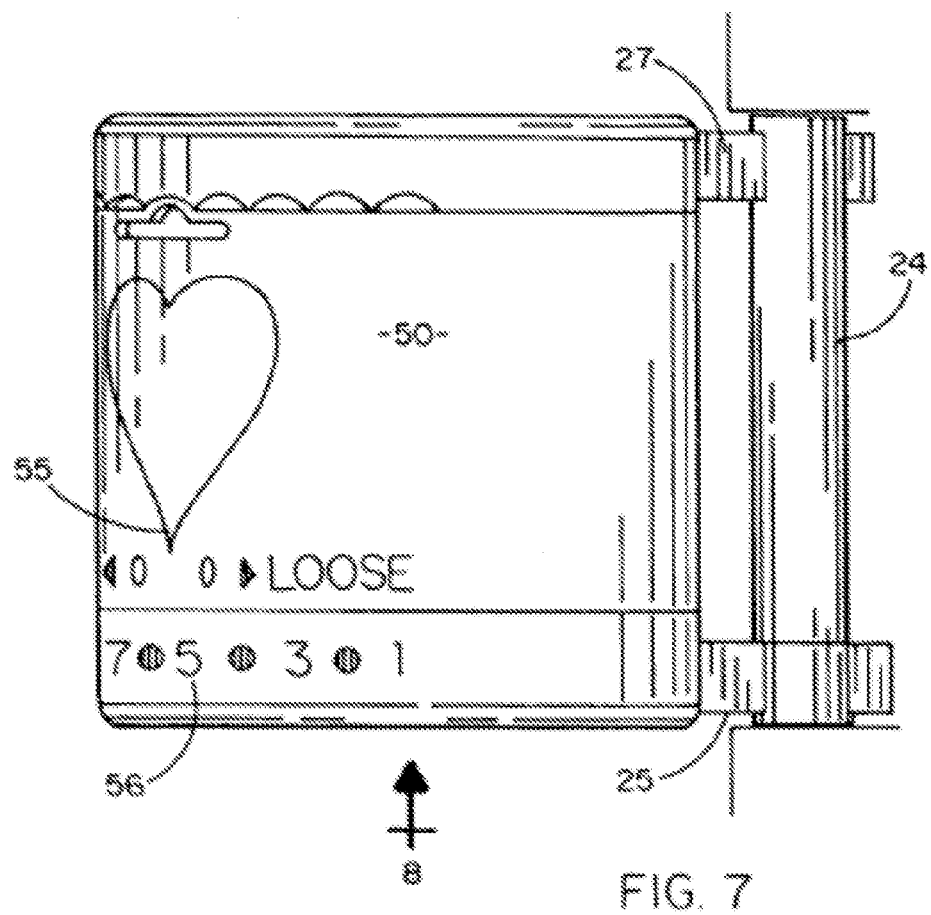
FIGS. 7 and 8 are views similar to FIGS. 5 and 6, respectively, but showing the assembly in a more tightened or closed configuration.
Figure 8:
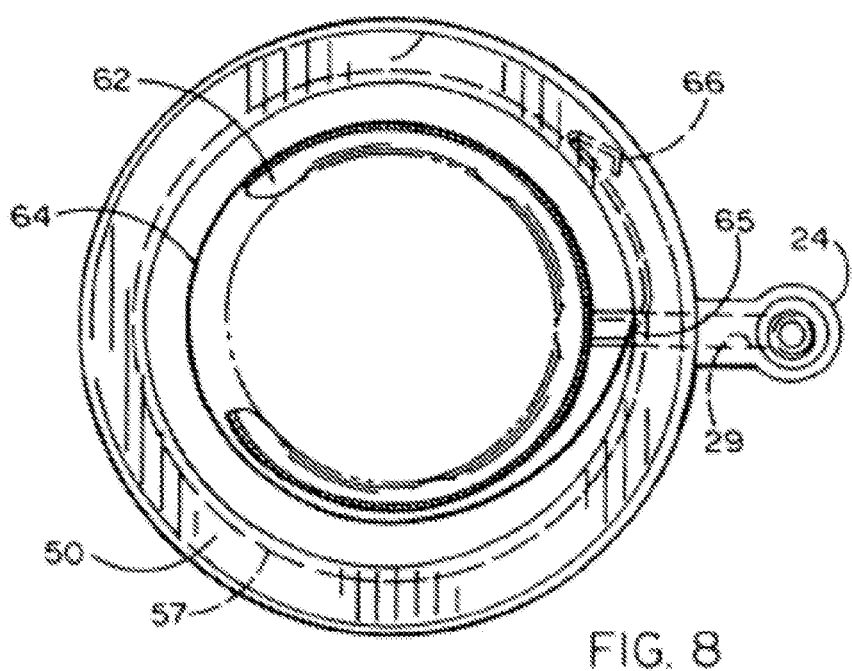

The ring 57 interior 28 encircles cuff 62 and a pull-tab 64. Tab 64 terminates in a tab end 66 which is routed through a slit 65 along the inner surface of fixed ring 57 and is retained within the inner surface of adjustment ring 50. FIGS. 6 and 8 show two distinct cuff adjustment positions wherein FIG. 6 corresponds to a fully opened cuff configuration and FIG. 8 to a more tightened or collapsed cuff configuration. It will be noted that the tab end 66 extends further through slot 65 in FIG. 8 than in FIG. 6. It will also be noted that ring 50 pointer 55 is positioned opposite indexing numeral 6 in FIG. 7 and opposite numeral 1 in FIG. 5.

Referring to FIGS. 9 and 10, it will be seen that finger cuff 62 is adhered to a pull-tab 64, the latter extending about twice the length of cuff 62 and terminating in tab end 66. A shoulder 67 provides a travel limit through slit 65 of ring 57. Air tube 29 is connected to cuff 62 through tab 64. Tab 64 is preferably a flexible transparent plastic film-like material. Thus it will now be seen that the cylinder assembly 22 provides a readily adjustable finger cuff assembly which upon rotation of ring 50 permits selective variation in the engagement of the cuff with fingers of different diameters.

It will be understood that the disclosed embodiments may be readily modified while having advantageous features thereof. Therefore the scope hereof is not to be limited by the disclosure, but by the appended claims.

We claim:

1. A finger cuff apparatus for selective occlusion of finger blood vessels for measuring blood pressure by inflation and deflation of an air inflatable cylindrical finger cuff to alter the diameter of the cuff in response to air pressure applied to the cuff, the apparatus being adjustable to manually vary the diameter of the cuff to accommodate different diameter fingers; the apparatus comprising:

an inflatable finger cuff having an air tube affixed to a source of controlled air pressure and wrapped into a cylindrical configuration within a pair of coaxial hollow rings of fixed diameters, one stationary and the other a rotatable ring;

a pull-tab adhered to the finger cuff along its entire length and having a tab end extending beyond the finger cuff through a slit in the stationary ring and into a retaining member in said rotatable ring;

wherein rotation of the rotatable hollow cylindrical ring relative to the stationary ring pulls or pushes said pull-tab to alter the shape of the finger cuff, both of said rings remaining unchanged relative to one another during the measurement of blood pressure.

2. The apparatus recited in claim 1 further comprising an indexing flange and a pointer on said rotatable ring for indicating a number corresponding to the rotatable ring position.

3. The apparatus recited in claim 1 further comprising a locking flange for retaining said rotatable ring in a selected position.

4. The apparatus recited in claim 1 further comprising a computer mouse having an accessible interior compartment for storing said finger cuff.

5. The apparatus recited in claim 1 further comprising a computer mouse having at least one air flow port for receiving said air tube of said finger cuff.

6. A manually adjustable finger cuff assembly for use with a blood pressure measurement device wherein a users finger is inserted into a cylindrical finger cuff for selective occlusion of blood flow in the users finger; the finger cuff assembly comprising:

an air inflatable finger cuff configured as a hollow cylinder having an adjustable diameter which is controlled by a pull tab adhered to said cuff and having a tab end;

a pair of co-axial cylindrical rings of fixed diameters, one ring stationary and one ring rotatable, said tab end of said pull tab being threaded between said stationary and rotatable rings with said finger cuff residing within said stationary ring so that rotation of said rotatable ring pulls or pushes said tab end to adjust said finger cuff cylinder diameter according to the size of a user's finger, both of said rings remaining unchanged relative to each other during measurement of blood pressure.

7. The assembly recited in claim 6 further comprising an indexing flange and a pointer on said rotatable ring for indicating a number corresponding to the adjusted rotatable ring position relative to said stationary ring.

8. The assembly recited in claim 6 further comprising a locking device for retaining the rotatable ring in an adjusted position.

9. The assembly recited in claim 6 further comprising a computer mouse having an accessible interior compartment for storing said finger cuff.

10. The assembly recited in claim 6 further comprising a computer mouse having at least one air flow port for connection to said inflatable finger cuff.

* * * * *